(12) United States Patent
Lee

(10) Patent No.: US 9,782,235 B2
(45) Date of Patent: Oct. 10, 2017

(54) IMPLANT SURGICAL GUIDE APPARATUS

(71) Applicant: ACRODENT CO., LTD, Gimhae-si, Gyeongsangnam-do (KR)

(72) Inventor: Jun Ho Lee, Geoje-si (KR)

(73) Assignee: ACRODENT CO., LTD, Gimhae-si, Gyeongsangnam-Do (KR)

( * ) Notice: Subject to any disclaimer, the term of this patent is extended or adjusted under 35 U.S.C. 154(b) by 0 days.

(21) Appl. No.: 15/463,258

(22) Filed: Mar. 20, 2017

(65) Prior Publication Data
US 2017/0189136 A1 Jul. 6, 2017

Related U.S. Application Data

(63) Continuation of application No. 14/357,891, filed as application No. PCT/KR2013/002669 on Apr. 1, 2013, now Pat. No. 9,636,190.

(30) Foreign Application Priority Data

Apr. 2, 2012 (KR) .......................... 10-2012-0034132
Apr. 4, 2012 (KR) .......................... 10-2012-0035031

(51) Int. Cl.
| | |
|---|---|
| A61C 1/08 | (2006.01) |
| A61C 3/04 | (2006.01) |
| A61C 3/02 | (2006.01) |
| A61C 8/00 | (2006.01) |
| A61C 8/02 | (2006.01) |
| A61B 50/20 | (2016.01) |
| A61B 17/17 | (2006.01) |
| A61C 19/02 | (2006.01) |
| A61B 17/16 | (2006.01) |
| A61B 50/30 | (2016.01) |

(52) U.S. Cl.
CPC .......... *A61C 1/084* (2013.01); *A61B 17/1673* (2013.01); *A61B 17/176* (2013.01); *A61B 50/20* (2016.02); *A61C 3/02* (2013.01); *A61C 3/04* (2013.01); *A61C 8/0006* (2013.01); *A61C 8/0089* (2013.01); *A61C 19/02* (2013.01); *A61B 17/162* (2013.01); *A61B 17/1633* (2013.01); *A61B 50/30* (2016.02)

(58) Field of Classification Search
CPC ......... A61C 1/084; A61C 3/04; A61C 8/0006; A61C 8/0089; A61C 19/02; A61B 17/1673; A61B 17/176
USPC .................... 433/50, 51, 68, 72, 74, 75, 165
See application file for complete search history.

(56) References Cited

U.S. PATENT DOCUMENTS

| | | | |
|---|---|---|---|
| 7,429,175 B2* | 9/2008 | Gittelson | A61C 1/084 433/173 |
| 7,572,125 B2* | 8/2009 | Brajnovic | A61C 1/084 433/75 |

(Continued)

*Primary Examiner* — Pedro Philogene
*Assistant Examiner* — David C Comstock
(74) *Attorney, Agent, or Firm* — Kile Park Reed & Houtteman PLLC

(57) ABSTRACT

An implant surgical guide apparatus includes a bone pen which is standardized by various diameters based on mesio-distal distances of natural teeth so that an implant can be placed at the center of a prosthetics, and comprises a cup having a rotatably symmetrical shape and a pen coupled to the cup and drilling into an alveolar bone so that the implant can be guided to a position with an angle as desired by an operator when the implant is placed in the alveolar bone corresponding to tooth loss.

3 Claims, 16 Drawing Sheets

(56) References Cited

U.S. PATENT DOCUMENTS

2004/0219477 A1* 11/2004 Harter .................... A61C 1/084
 433/75
2009/0286201 A1* 11/2009 Choe ...................... A61C 1/084
 433/165

* cited by examiner

IMPLANT SURGICAL GUIDE APPARATUS

CROSS REFERENCE TO RELATED APPLICATIONS

This application is a continuation application of U.S. patent application Ser. No. 14/357,891, filed May 13, 2014 (now pending), the disclosure of which is herein incorporated by reference in its entirety. The U.S. patent application Ser. No. 14/357,891 is a national entry of International Application No. PCT/KR2013/002669, filed on Apr. 1, 2013, which claims priority to Korean Application Nos. 10-2012-0034132 and 10-2012-0035031 filed on Apr. 2, 2012 and Apr. 4, 2012, respectively, the entire contents of which are incorporated herein by reference.

TECHNICAL FIELD

The present invention relates to a bone pen, a bone pin, a bone pen set, a bone pin set and a bone pen kit including the same and an initial drill, and more particularly to a bone pen, a bone pin, a bone pen set, a bone pin set and a bone pen kit including the same and an initial drill, which have shapes most similar to the mesiodistal diameter as one of common characteristics of a tooth targeted for treatment, can do marking and drilling at a position closest to the center of the mesiodistal diameter, harvest bone and in which the bone pen set has a similar structure to a prosthesis or a tooth.

BACKGROUND ART

Recently, an implant procedure has been generalized to substitute tooth loss. Typically, such an implant procedure refers to a series of procedures where a fixture is installed after drilling an alveolar bone, and various abutments and the fixture are fixed to thereby finally fasten a prosthesis to the fixture. In this procedure, if there is interference with the alveolar bone or the gingiva, a procedure of removing it may be further added.

In such a series of operations, various instruments and methods have been used. The present invention relates to instruments for implant placement, needed for surgical operations in procedures of cutting a gingiva and drilling the alveolar bone to install the fixture.

First, methods of centering a target tooth in order to perform the implant procedure have been disclosed by the present applicant in Korean Patent Publication No. 10-2011-106573 and U.S. Pat. No. 6,869,282.

Also, an instrument for harvesting a bone while drilling the alveolar bone or harvesting an autogenous bone by perforating a cortical bone has been disclosed in Korean Patent No. 10-0796907.

Conventional instruments for centering the target tooth or harvesting a bone have a problem of a simple structure without considering the size, shape, etc. of the tooth targeted for treatment.

Also, there is concern about determining the center, etc. of each target tooth by a user's experience or the like if many target teeth are lied on one after another.

Further, in the procedure including successive operations, it is inconvenient since the tools are different in maker, type, kind, etc. and there is a problem that very various kinds of tools are needed.

DISCLOSURE

Technical Problem

It is an aspect of the present invention to provide a bone pen, a bone pin, a bone pen set, a bone pin set and a bone pen kit including the same and an initial drill, which have a shape and size corresponding to an average shape of each target tooth.

It is another aspect of the present invention to provide a bone pen, a bone pin, a bone pen set, a bone pin set and a bone pen kit including the same and an initial drill, which harvest a bone while easily and conveniently marking and drilling the center of the target tooth.

It is still another aspect of the present invention to provide a bone pen, a bone pin, a bone pen set, a bone pin set and a bone pen kit including the same and an initial drill, which are standardized to be optimized corresponding to various sizes of the target tooth.

It is still another aspect of the present invention to provide a bone pen, a bone pin, a bone pen set, a bone pin set and a bone pen kit including the same and an initial drill, which are convenient for operations of a series of target teeth.

It is still another aspect of the present invention to provide a bone pen, a bone pin, a bone pen set, a bone pin set and a bone pen kit including the same and an initial drill, in which height of a prosthesis and drilling depth of a fixture or the like can be easily determined.

It is still another aspect of the present invention to provide a bone pen, a bone pin, a bone pen set, a bone pin set and a bone pen kit including the same and an initial drill, in which the minimum set of instruments corresponding to serial operations and various target teeth is provided to thereby improve convenience and economic feasibility.

It is still another aspect of the present invention to provide a bone pen, a bone pin, a bone pen set, a bone pin set and a bone pen kit including the same and an initial drill, in which damage to a gingiva or an alveolar bone is minimized while drilling or harvesting a bone.

It is still another aspect of the present invention to provide a bone pen, a bone pin, a bone pen set, a bone pin set and a bone pen kit including the same and an initial drill, in which a surgical operation is improved in reliability, accuracy and economic feasibility.

Technical Solution

An aspect of the present invention is achieved by providing a bone pen comprising: a pen which is coupled to a user's handpiece and comprises a drill section provided at an end portion thereof to drill to an alveolar bone; a cup which has an accommodating space to hold therein bone particles harvested during the drilling alveolar bone, has an outer diameter corresponding to a mesiodistal diameter of a patient's tooth targeted for treatment, and coupled to the pen so that the accommodating space can surround the drill section; and a spring which is supported at one side of the pen and elastically supports the cup with regard to the pen, wherein the drill section of the pen is positioned at a central axis line of the cup, maintained as being positioned at a mesiodistal diameter center of the tooth targeted for treatment, and guided for drilling.

Another aspect of the present invention is achieved by providing a bone pin comprising a pin which is coupled to a user's handpiece and has a size corresponding to the drill section so as to be coupled with a hole drilled by a drill section provided at an end portion thereof to drill to an alveolar bone; and a cap which is provided to have an outer diameter corresponding to a mesiodistal diameter of a patient's tooth targeted for treatment, and coupled to the pin as being elastically supported by the pin and movable with regard to the pin.

The cap may include an indicator provided to measure height of a prosthesis of the target tooth corresponding to the height of the pin in the state that the pin is moved with regard to the cap as the pin is coupled to the drilling hole of the alveolar bone by the pen and the oppositely occluded tooth presses the pin.

Another aspect of the present invention is achieved by providing a bone-pen bone-pin set, in which the bone pens or the bone pins are sorted into a plurality of standards segmented corresponding to a patient's tooth.

The bone pens or the bone pins may have outer diameters of 6 mm, 7 mm, 8 mm, 9 mm and 10 mm.

There may be further provided an initial drill which performs a drilling operation for installing a fixture based on a hole of an alveolar bone formed by the bone pen The drilling depth of the initial drill may be based on height measured by an indicator marked on the bone in a state that the bone pin coupled to a target tooth is occluded with an opposite tooth.

Advantageous Effects

In accordance with an aspect of the present invention, there are provided a bone pen, a bone pin, a bone pen set, a bone pin set and a bone pen kit including the same and an initial drill, which have a shape and size corresponding to an average shape of each target tooth, harvest a bone while easily and conveniently marking and drilling the center of the target tooth, and are standardized to be optimized corresponding to various sizes of the target tooth.

Also, in accordance with an aspect of the present invention, there are provided a bone pen, a bone pin, a bone pen set, a bone pin set and a bone pen kit including the same and an initial drill, which are convenient for operations of continuous target teeth, and easily determine height of a prosthesis and drilling depth of a fixture or the like.

Also, in accordance with an aspect of the present invention, there are provided a bone pen, a bone pin, a bone pen set, a bone pin set and a bone pen kit including the same and an initial drill, in which the minimum set of instruments corresponding to serial operations and various target teeth is provided to thereby improve convenience and economic feasibility, damage to a gingiva or an alveolar bone is minimized while drilling or harvesting a bone, and a surgical operation is improved in reliability, accuracy and economic feasibility.

BEST MODE

Embodiments of a bone pen, a bone pin, a bone pen set, a bone pin set and a bone pen kit including the same and an initial drill (hereinafter, referred to as a 'bone pen kit', 400) according to the present invention will be described in detail with reference to FIGS. 1 to 8B.

Figure 1:
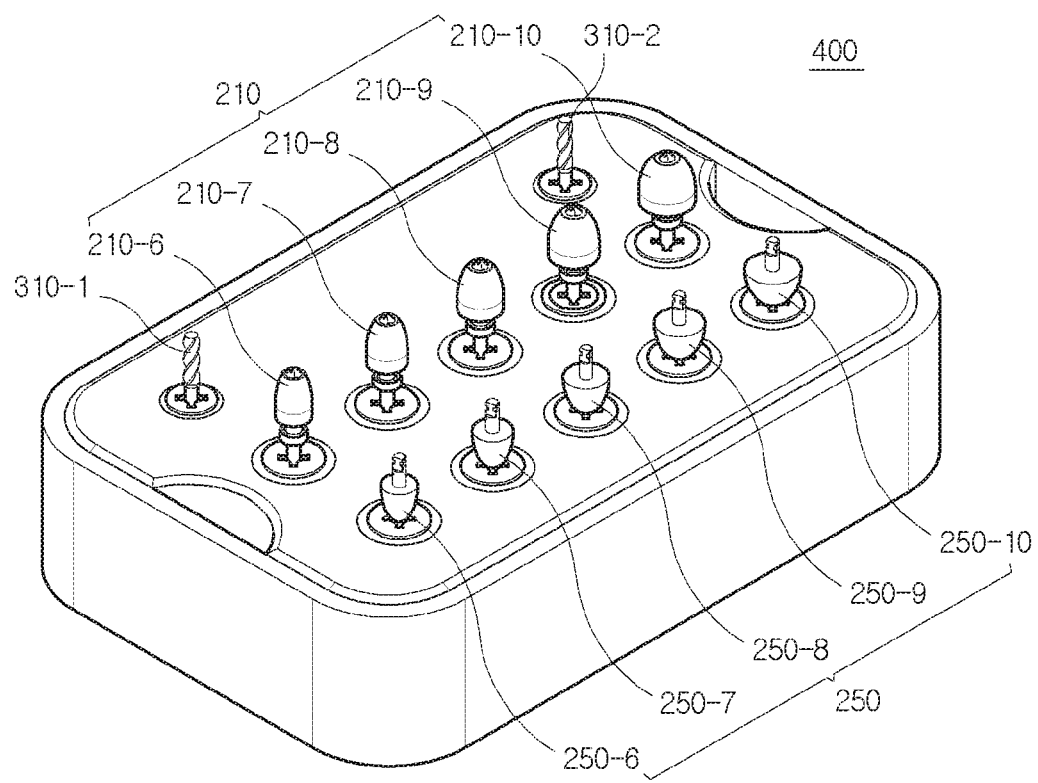
FIG. 1 is a perspective view of a bone pen kit according to an embodiment of the present invention.
Figure 2A:
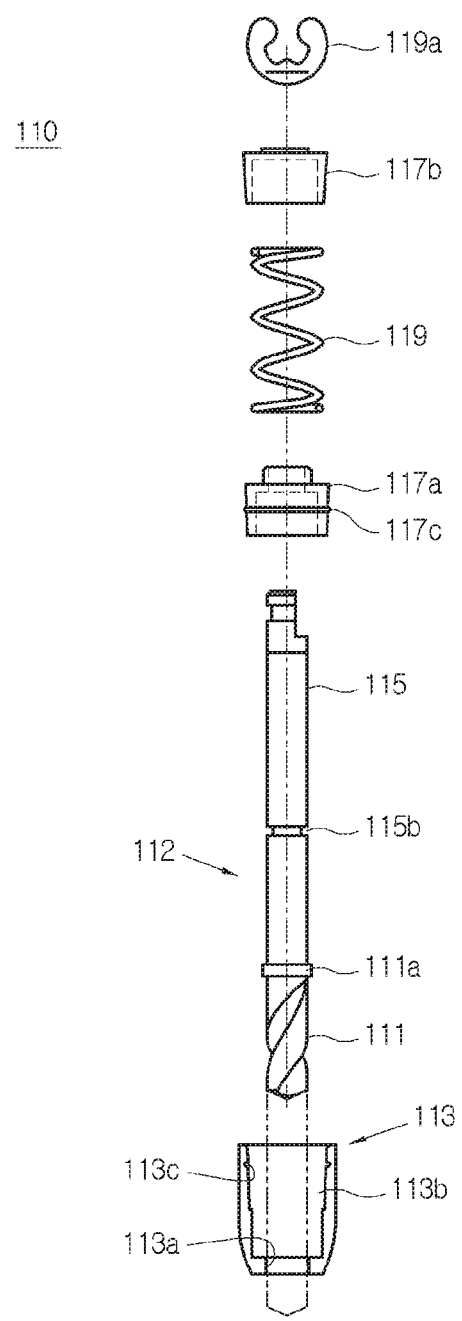
FIGS. 2A, 2B and 2C are an exploded perspective view, an exploded perspective view and a front view of a bone pen, a bone pin and an initial drill, respectively.
Figure 2B:
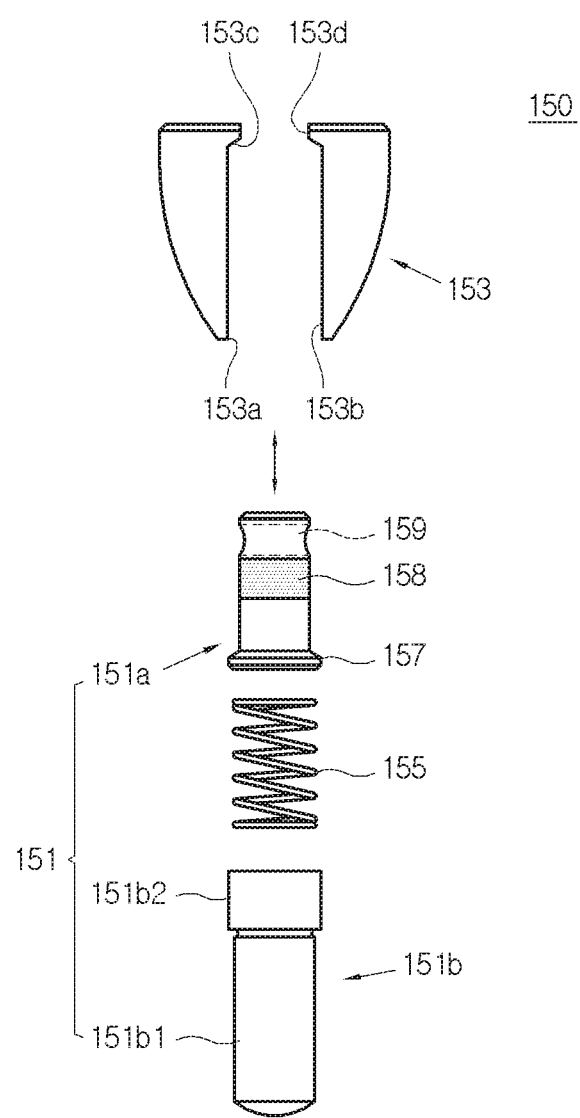
Figure 2C:
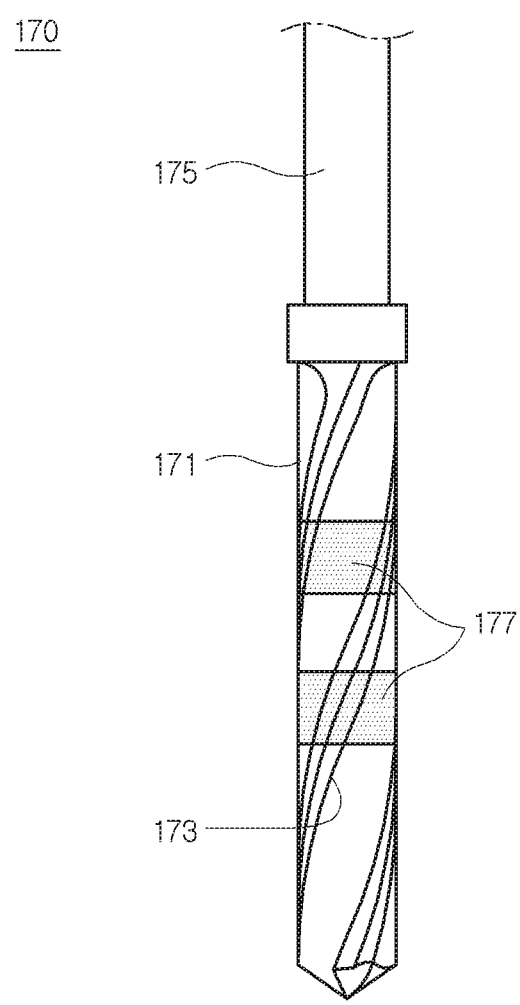
Figure 8A:
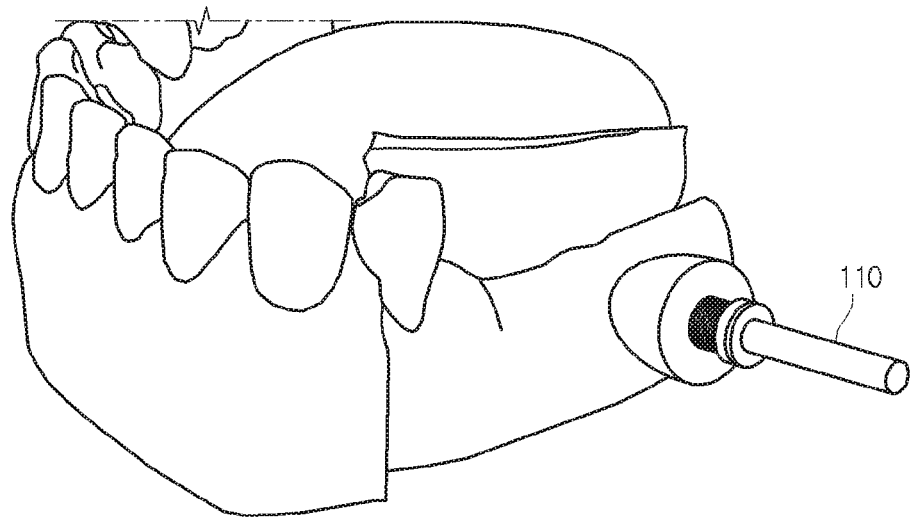
FIGS. 8A and 8B are schematic views for explaining examples of performing a guided bone regeneration procedure according to an embodiment of the present invention.
Figure 8B:
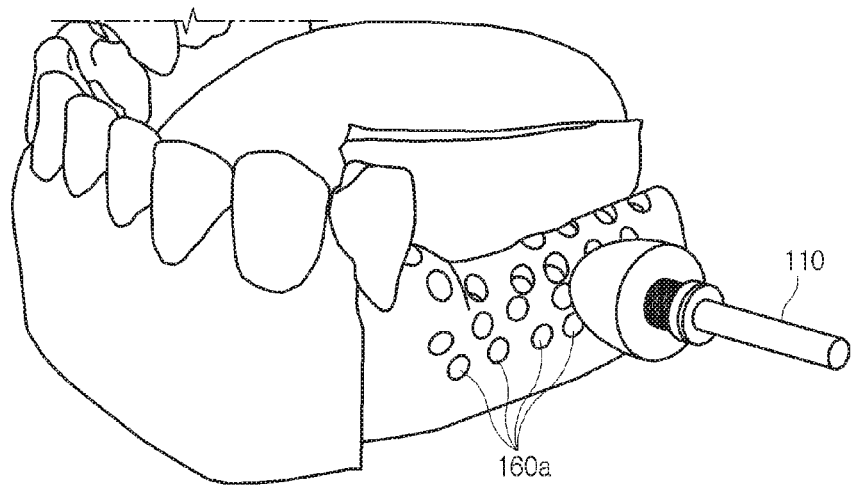

FIG. 1 is a perspective view of a bone pen kit according to an embodiment of the present invention, FIGS. 2A, 2B and 2C are an exploded perspective view, an exploded perspective view and a front view of a bone pen, a bone pin and an initial drill, respectively, FIGS. 3A to 7 are schematic views for explaining examples of using the bone pen kit, and FIGS. 8A and 8B are schematic views for explaining examples of performing a guided bone regeneration procedure according to an embodiment of the present invention.

First, a bone pen kit 400 includes a bone pen set 210, a bone pin set 250 and an initial drill set 310.

The bone pen set 210 or the bone pin set 250 includes a plurality of standardized bone pens 110 or bone pins 150.

The bone pen 110 as shown in FIGS. 1 and 2A includes a drill section 111 having a groove for removing or drilling an alveolar bone of a target tooth, and a coupling section 115 extended from the drill section 111 and coupled to a handpiece.

Further, the bone pen 110 includes a cup 113 coupled to surround the drill section 111 and internally formed with an accommodating space 113b for accommodating a harvested bone, and a pen 112 having a long shape to which the cup 113 is coupled.

The bone pen 110 includes a lower stopper 117b coupling with the cup 113 and supporting a pen spring 119, the pen spring 119 elastically supporting the cup 113, an upper stopper 117a supporting the pen spring 119 at a position opposite to the lower stopper 117b with the pen spring 119 therebetween, and a snap ring 119a preventing movement of the upper stopper 117a.

The pen 112 includes a drill section 111 formed with a groove in a lower end portion thereof to remove the alveolar bone, a coupling section 115 placed at an upper side and coupled to the handpiece, and a neck 115b provided in the coupling section 115 and the drill section 111.

A projection 111a for preventing movement of the lower stopper 117b and the neck 115b coupling with the snap ring 119a are respectively provided in between the drill section 111 shaped like a bar and the coupling section 115 shaped like a stick.

The cup 113 has an outer diameter corresponding to a mesiodistal diameter of the target tooth, is tapered toward the drill section 111 while forming a smooth curve, and formed with a cup opening 113a in a central axis line to which the drill section 111 is coupled.

Meanwhile, to facilitate coupling between the cup 113 and the lower stopper 117b, the inside of the cup 113 and the lower stopper 117b are respectively formed with the holding portion 113c and the protrusion 117c so that they can snap to be coupled each other, thereby facilitating detachable coupling of the cup 113.

That is, the central axis line of the bone pen 110 is formed so that the drill section 111 can be coupled to the central axis line of the cup 113 having the mesiodistal diameter of the target tooth. Therefore, it is easy and convenient for a user to perform a drilling operation while positioning the bone pen 110 at the center of the target tooth, thereby carrying out a three-dimensional (3D) marking operation for the implant placement.

Thus, if a user drills the target tooth or the like, the cup 113 moves up and down toward the coupling section 115 against pressure of the pen spring 119 as deep as drilled by the drill section 111, so that the bone harvested in the drilling procedure can be collected in the accommodating space 113b of the cup 113 along the groove of the drill section 111.

The cup 113 is shaped to have the same diameter from a portion of coupling with the lower stopper 117b, corresponding to the mesiodistal diameter of the target tooth, up to a certain height, and shaped describing a gentle parabola from the portion having the same diameter up to the cup opening 113a like a tooth that tapers toward its root. Such a shape has advantage of minimizing damage of the alveolar bone in the vicinity of the drilling operation even though the cup 113 rotates like the drill section 111. If the cup has a large bottom or a smoothly narrowed curve, the cup may contact wide regions around the drilled alveolar bone when the cup rotates along with the drill section. Occasionally, the lower rotational part of the cup may be enlarged and damage the surrounding gingiva. That is, the lower end portion of the cup 113 according to an embodiment of the present invention, which is relatively similar to the shape of the tooth, is so sharp that a region occupied with the cup 113 rotating in the vicinity of the alveolar bone desired to be drilled can be minimized even though the cup 113 rotates together with the drill section 111. Thus, it is possible to minimize the damage to the gingiva or alveolar bone due to the bone harvest.

As necessary, the cup 113 may be provided with a rotation preventing means (not shown) supported in the alveolar bone, the gingiva or the handpiece so that the cup 113 cannot rotate even when the drill section 111 rotates.

On the other hand, as necessary, the cup 113 may be provided with a spiral groove (not shown) so that cooling water on the outer surface of the cup 113 rotating due to the drilling operation of the drill section 111 can move toward the center of the drill section 111.

In the operation for the implant placement, the bone pen 110 has an advantage of not only marking and drilling a position for a fixture or the like prior to an operation of the initial drill 170 (to be described later) that performs the drilling operation for coupling the fixture or the like but also collecting an autologous bone harvested in this operation. That is, 3D positions for determining the drilling position for the typical implant placement may include a mesiodistal position, a buccolingual position, and a vertical depth to be drilled.

Among the 3D positions, the center of the mesiodistal diameter of the target tooth is simply, conveniently and automatically determined by the bone pen 110 based on the center of the drill section coupled to the central axis line of the cup 113.

Further, among the 3D positions, the buccolingual center position of the target tooth may be intuitively determined by naked eyes or tactile impression in light of a dentist or the like user having clinical experience while the gingiva is cut and opened.

Figure 2D:
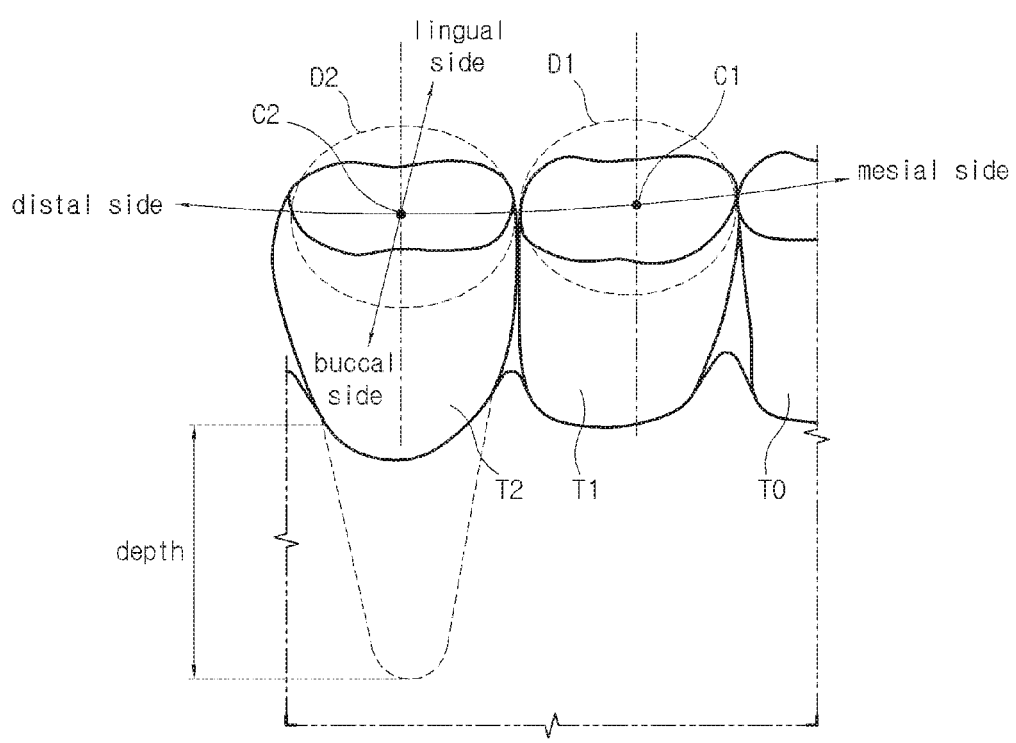
FIG. 2D is a schematic view for explaining an operation of determining 3D positions of a target tooth using a bone pin.

Below, the procedure of determining the 3D positions of the target tooth using the bone pen 110 according to an embodiment of the present invention will be described with reference to FIG. 2D.

First, suppose that the implant procedure is performed in the state that there is a patient's adjacent tooth T0 and target teeth T1 and T2 respectively adjacent thereto are lost. The mesiodistal diameter "D1" of T1 is simply obtained based on a desired ideal set of teeth, the standard of the bone pen 110 most approximate to the mesiodistal diameter "T1" is selected and the cup 113 is positioned adjacent to the adjacent tooth T0, thereby determining the center of the target tooth in the mesiodistal direction. Then, a user determines the buccal and lingual directional center from the alveolar bone shown by making an incision and retraction of the gingiva through his/her naked eyes or tactile impression, thereby positioning the drill section 111 at the buccal and lingual directional center (refer to "C1" of FIG. 2D) to perform drilling and marking. Thus, it is very easy and convenient for a user to determine the center (refer to "C1" of FIG. 2D) of the target tooth in the mesiodistal direction and the buccolingual direction through the bone pen 110 according to an embodiment of the present invention.

As shown in FIG. 2B, the bone pin 150 includes a pin body 151 having a lower pin 151b and an upper pin 151a shaped like a bar corresponding to the size of the bone pen 110, a cap 153 corresponding to the shape of the cup 113 of the bone pen 110, and a cap spring 155 elastically supporting the cap 153. The cap spring 155 has a first side supported on a top side of the lower pin 151b and a second side supported on a bottom side of the upper pin 151a.

Further, the cap 153 includes upper and lower cap openings 153a, 153d penetrated to respectively couple with the lower pin 151b and the upper pin 151a, and a cap holding portion 153b communicating with an inner surface of the lower cap opening 153 of the cap so that the pin protrusion 151b1 of the lower pin 151d can be forcibly fitted and firmly coupled thereto along the inner surface of the penetrated hole. Thus, the lower pin 151b is maintained as being coupled to a lower side of the cap 153 and supports the lower side of the cap spring 155, so that the cap spring 155 can elastically support the upper pin 151a with respect to the cap 153 or the lower pin 151b.

The upper pin 151a is shaped like a stick, and coupled to and retractable through the upper cap opening 153d of the cap 153. Further, the upper pin 151a includes a pin projection 157 in the bottom thereof not to come out through the cap projection 153c, an indicator 158 positioned at a proper height from the top thereof and having distinctive color or the like, and an upper through hole 159 to which a thread or the like may be coupled for convenience in use.

The lower pin 151b is shaped like a stick and includes an alveolar bone hole coupling section 151b1 having a size corresponding to the size of the drill section 111 and coupled to the alveolar bone hole 160 drilled and marked by the bone pen 110, and a pin protrusion 151b2 provided at an upper portion and having a predetermined height to be engaged with the cap holding portion 153b. Thus, the lower pin 151b has one side coupled to the alveolar bone hole 160 and the other side coupled to the cap 153.

Therefore, if the lower pin 151b is coupled to the alveolar bone hole 160 drilled by the drill section 111 of the bone pen 112, the bottom of the cap 153 is supported by the alveolar bone, and the upper pin 151a coupled to the top of the cap 153 is externally pressed by a tooth or the like opposite to the target tooth, it is possible to easily measure the height of the prosthesis of the target tooth by naked eyes while the upper pin 151a moves with regard to the cap 153.

Thus, if the bone pin 150 is coupled to the position drilled by the bone pen 110, a user may recognize as if the target tooth is present since the size of the cap 153 corresponds to the mesiodistal diameter of the target tooth, and it is therefore very convenient when the centering position of the tooth adjacent to the target tooth is set up or marked for a surgical operation.

That is, it is easy and convenient to determine the drilling depth as one among the foregoing 3D positions through the bone pen 110. Using the bone pen 110 and the bone pin 150 according to an embodiment of the present invention, the mesiodistal centering position, the buccolingual centering position, and the drilling depth are easily and conveniently determined and measured as the 3D positions when the drilling operation is performed in order to set up the initial position for the implant placement.

Below, an operation of determining the 3D positions of the target tooth through the bone pin 150 according to an embodiment of the present invention will be described with reference to FIG. 2D.

As mentioned above, if the implant procedure is performed in the state that there is a patient's adjacent tooth T0 and the target teeth T1 and T2 respectively adjacent thereto are lost, a user can very easily and conveniently determine the center of the target tooth in the mesiodistal and buccolingual directions (refer to "C1" of FIG. 2D) through the bone pen 110 according to an embodiment of the present invention.

If the center of the target tooth "T1" is easily set up and drilled by the drill section 111 and then the bone pin 150 is coupled and pressed to the alveolar bone hole 160 formed in the alveolar bone, it is easy to measure the height or the like of the prosthesis based on the height of the cap 153 and the indicator 158 in the state that the upper pin 151a moves with regard to the cap 153 and gets occlusion by the tooth occluded with the target tooth "T1", thereby easily determining the drilling depth of the initial drill 170 so that a user can finally implant a fixture or the like. Accordingly, it is easy and convenient to determine the 3D positions of the target tooth.

As compared with a conventional method based on a user's experience or using a complicated jig or the like, the present invention employs a reference point, i.e., the bone pen 110 and the bone pin 150 which are very convenient and simple and have reliability of a more precise position, and thus improve not only reliability of a surgical operation based on such convenience, simpleness and efficiency but also economic feasibility based on shortened time of the surgical operation.

Meanwhile, as shown in FIG. 1, the bone pen set 210 refers to that the bone pens 110 are classified and standardized corresponding to the mesiodistal diameters of patients having general permanent teeth. For example, the bone pens 110 according to the present invention are standardized in units of 1 mm considering that the general mesiodistal diameter is 10-6 mm. That is, according to an embodiment of the present invention, the cup 113 has an outer diameters of 6 mm (210-6), 7 mm (210-7), 8 mm (210-8), 9 mm (210-9), and 10 mm (210-10).

Here, the bone pen set 210 is standardized to have five steps by taking convenience, clinical experience, economic feasibility, etc. into account, but not limited thereto. As necessary, such standardization may be more simplified by decreasing the steps or more segmented by increasing the steps. In this exemplary embodiment, the outer diameter of the cup 113 is divided by five steps from 6 mm to 10 mm in consideration of a tolerance limit and the like that there is tolerance at a user's surgical operation even though the center is precisely set up, because the outer diameter has just a tolerance of 0.5 mm.

Like the bone pen set 210, as shown in FIG. 1, the bone pin set 250 refers to that the bone pins 150 are classified and standardized corresponding to the mesiodistal diameters of patients having general permanent teeth. For example, the bone pins 150 according to the present invention are standardized in units of 1 mm considering that the general mesiodistal diameter is 10-6 mm. That is, according to an embodiment of the present invention, the cup 113 has an outer diameters of 6 mm (210-6), 7 mm (210-7), 8 mm (210-8), 9 mm (210-9), and 10 mm (210-10).

Further, as shown in FIG. 2C, the initial drill 170 according to an embodiment of the present invention drills the alveolar bone hole 160 drilled by the bone pen 110 at a desired depth in order to implant the fixture. The initial drill 170 includes a body 171 for drilling the alveolar bone, a groove 173 formed in the body 171, a shank 175 coupled to the handpiece, and a marking portion 177 marked on the body 171 so that a user can be informed of drilled depth through naked eyes.

Thus, a user can perform the drilling operation as deep as desired using the initial drill 170 in consideration of the height of the prosthesis based on the height of the indicator 158 of the bone pin 150 or the like. Preferably, a drilling part of the body 171 of the initial drill 170 may have a diameter corresponding to the diameter of the pin body 151 of the bone pin 150 and the drill section 111 of the bone pen 110.

Here, the initial drill 170 may preferably have a diameter of 2.8 mm so as to be used in common for fixtures of various makers on the contrary to the outer diameter of the cap 153 or the cup 113, but not limited thereto.

Alternatively, the initial drill 170 may have a different diameter. That is, a drilling operation with a final drill for the fixtures of various makers may be performed by the initial drill 170.

As shown in FIG. 1, the bone pen kit 400 according to an embodiment of the present invention includes the bone pen set 210, the bone pin set 250 and the initial drill set 310.

Below, an example of using the bone pen kit 400 will be described with reference to FIGS. 3A and 8B. As necessary, the bone pen or the bone pen set, and the bone pin or the bone pin set may be used as being mixed with each other, and may be called a bone-pen bone-pin set.

Figure 3A:
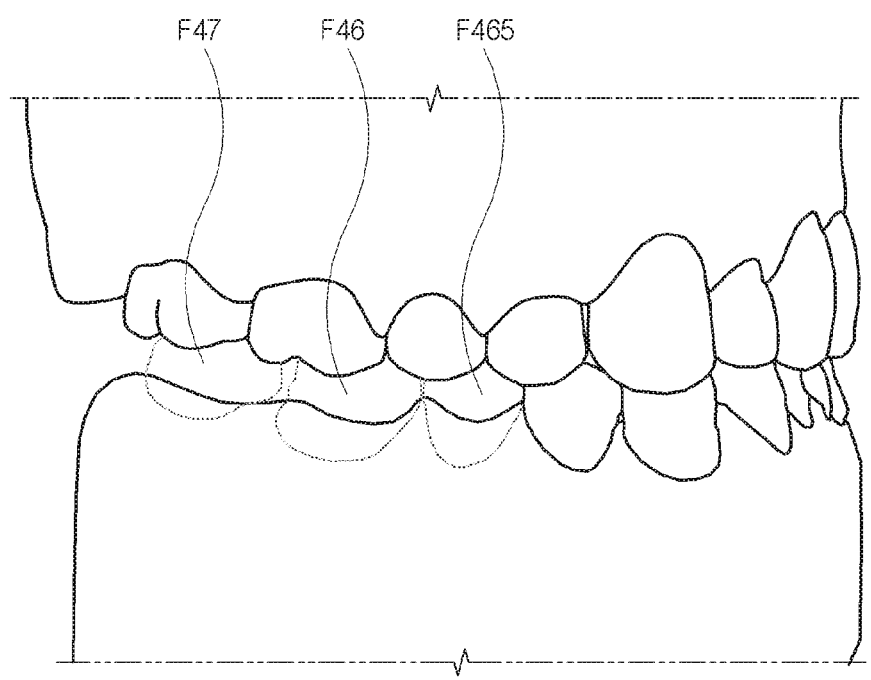
FIGS. 3A to 7 are schematic views for explaining examples of using the bone pen kit.
Figure 3B:
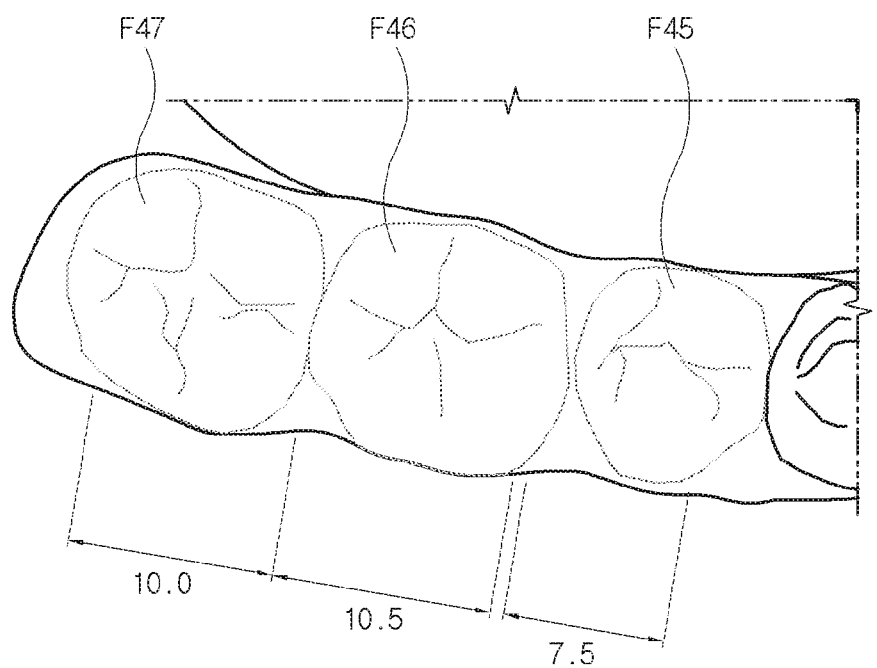

First, as shown in FIGS. 3A and 3B, suppose that a patient's teeth targeted for treatment need an implant procedure since mandibular right molars (the first molar 'T-45', the second molar 'T-46', and the third molar 'T-47') are all lost.

Further, suppose that the teeth targeted for treatment are measured by a user, i.e., an operator and show a result that the respective teeth T-45, T-46 and T-47 have mesiodistal diameters of 7.5 mm, 10.5 mm, and 10 mm, respectively.

Figure 4A:
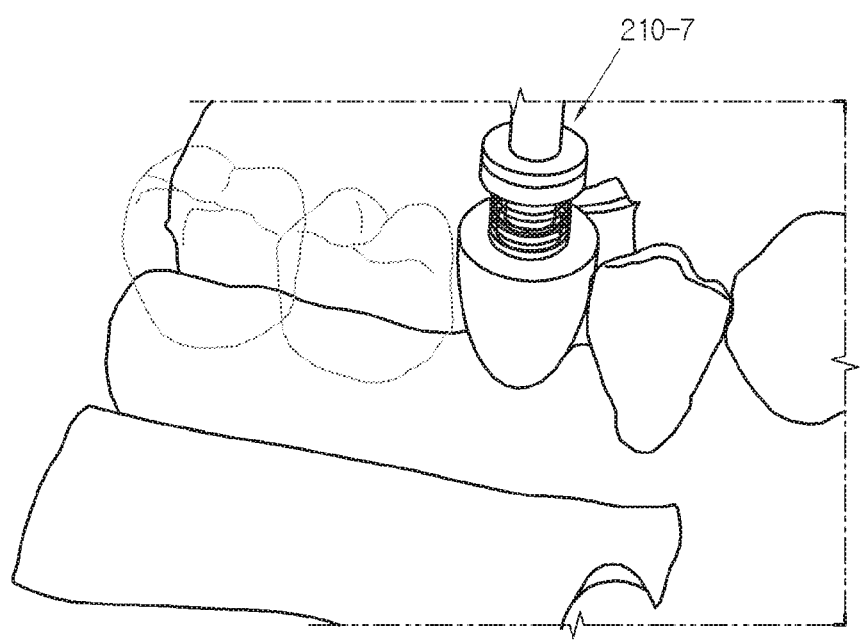
Figure 4B:
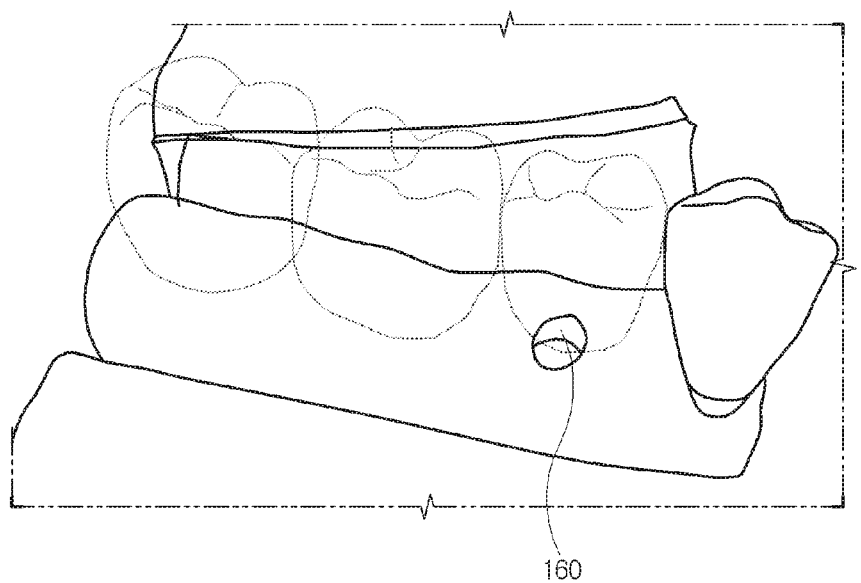

Thus, as shown in FIG. 4B, a user couples the bone pen 210-7 having a diameter of 7 mm corresponding to the first molar T-45 having the mesiodistal diameter of 7.5 mm to the handpiece, and places the cup 113 in the vicinity of the adjacent tooth and at the same time so that the central axis line of the drill section 111, i.e., the central axis line of the cup 113 can be aligned with the buccolingual center of the alveolar bone exposed by making a gingival incision, thereby drilling and marking the alveolar bone hole 160 through the operation of the handpiece while applying pressure in a vertical direction.

With this, as shown in FIG. 4B, the alveolar bone hole 160 may set up the 3D positions for the initial drill 170 since the alveolar bone is drilled at a depth lower than the depth of the initial drill 170 as a drilling operation for marking.

Figure 5A:
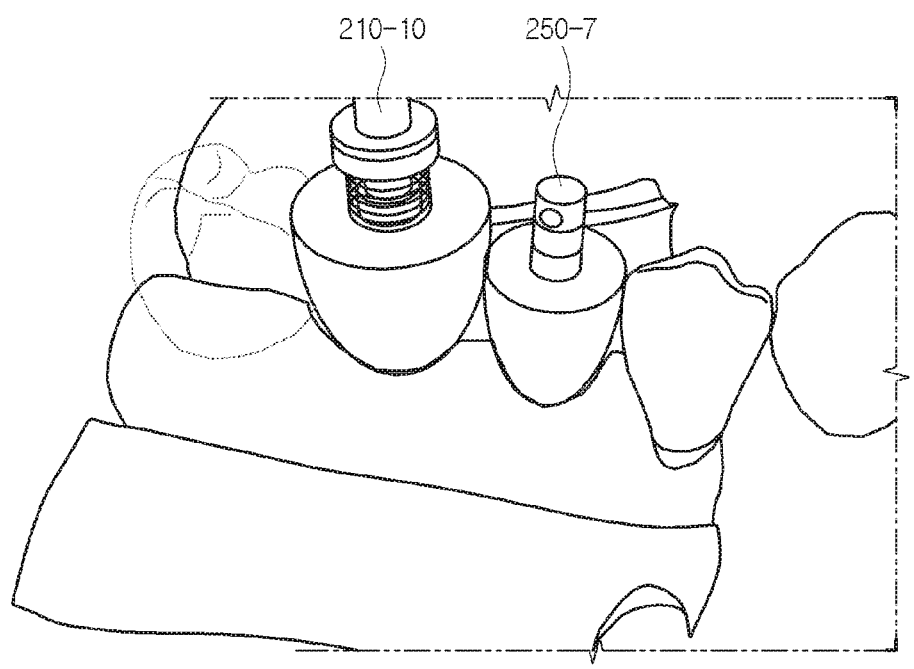

Further, as shown in FIG. 5A, the bone pin 250-7 having the diameter of 7 mm corresponding to the bone pen 110 having the diameter of 7 mm is coupled to the alveolar bone marked at the position of the first molar T-45.

In addition, the bone pen 210-10 having the diameter of 10 mm adaptive to the mesiodistal diameter of 10.5 mm is coupled to the handpiece for the marking operation of the second molar T-46 in a state similar to that the first molar crown is present due to the bone pin 250-7 coupled at the position of the first molar T-45, thereby determining the mesiodistal and buccolingual centers as described above, marking the alveolar bone hole of the second molar T-46, and coupling the bone pen 210-10 of 10 mm.

Figure 5B:
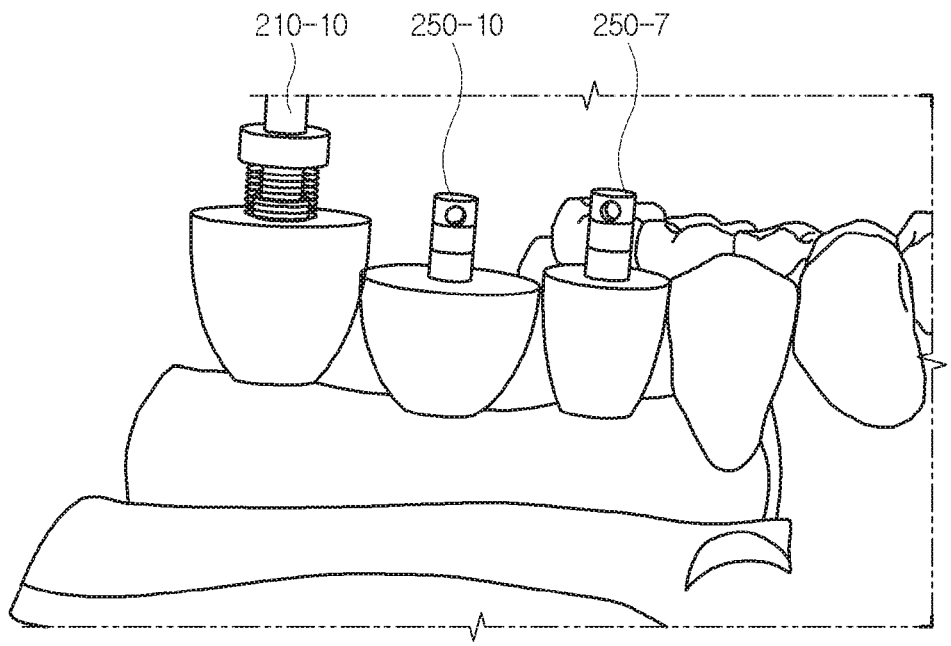

In such a manner, the marking operation is performed as shown in FIG. 5B at the position of the third molar T-47 by the bone pen 210-10 of the 10 mm in the state that the second bone pin 250-10 is coupled.

Figure 6A:
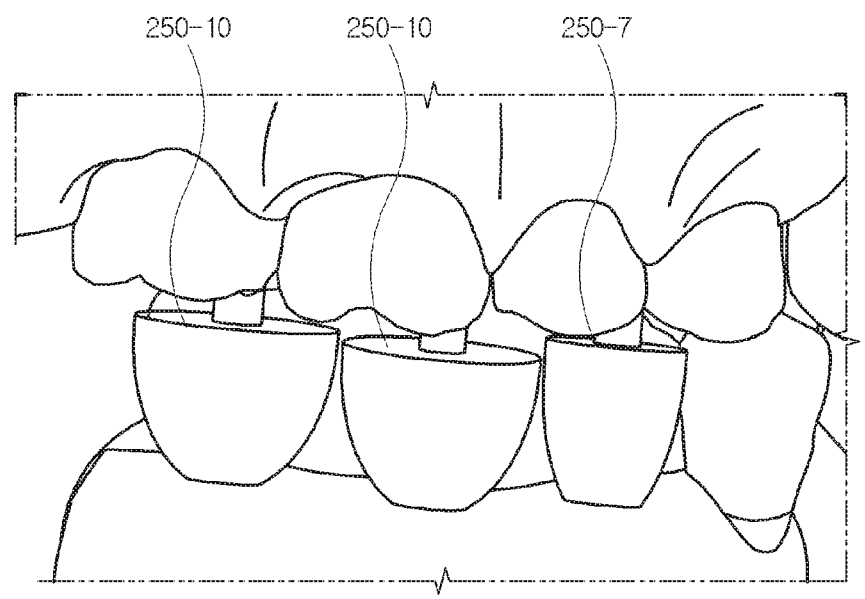
Figure 6B:
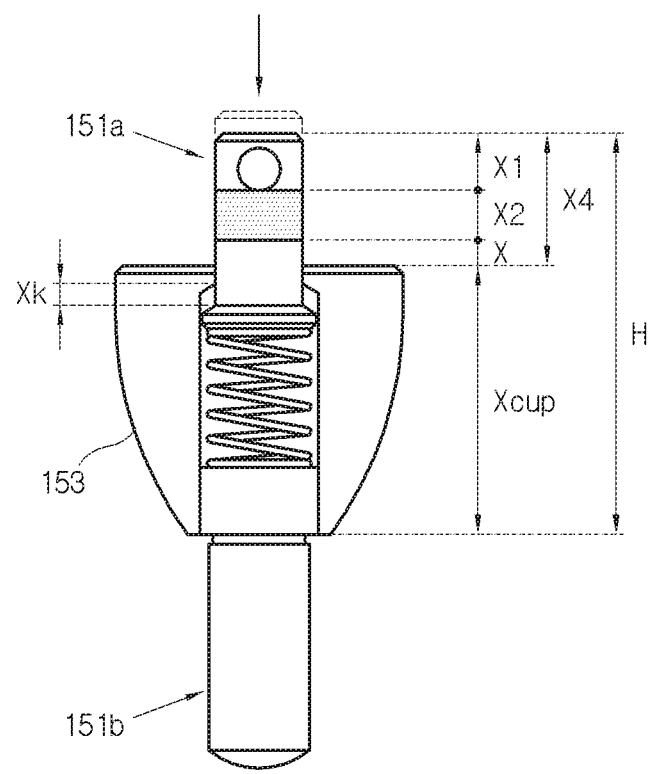
Figure 7:
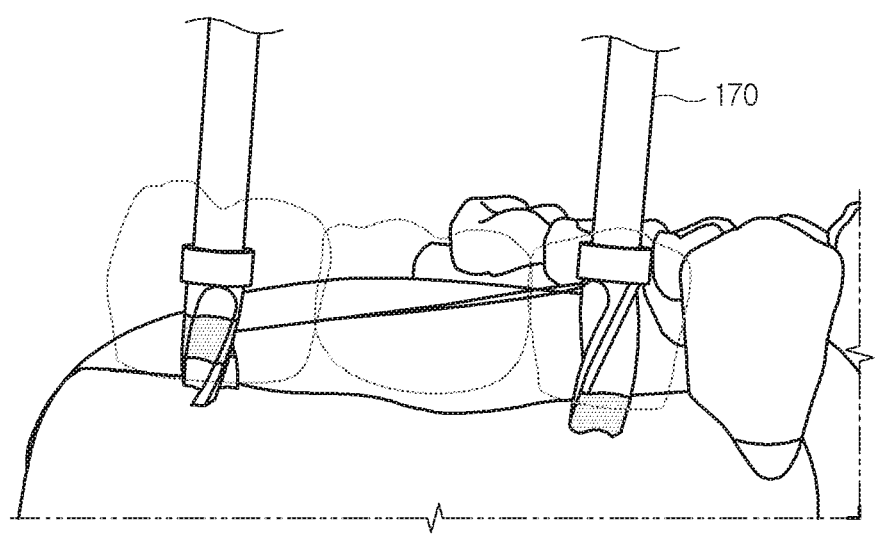

FIG. 6A illustrates that the bone pins 250-10 and 250-7 are inserted at their positions after the marking operations of the first molar T-45, the second molar T-46 and the third molar T-47 are completed, and then the opposing maxillary teeth press the bone pins 250-10 and 250-7 so that the pin body 151 can be pushed to the alveolar bone hole 160.

At this position, a user can be informed by the indicator 158 of the bone pin 150 through his/her naked eyes that the height of the prosthesis is equal to the height "H" of the top of the upper pin 151a in the lower end portion of the cap 153, i.e., "Xcup+X+X1+X2", thereby determining the drilling depth for installing the fixture in accordance with the height of the prosthesis. Here, the decreased length of the cap spring 155 is "Xk". In other words, a user is previously informed of heights "Xcup, X1 and X2" of respective parts of the bone pin 150, and easily determines the height "X" from the lower end of the indicator 158 to the upper end portion of the cap 153 through his/her naked eyes, thereby easily obtaining a vale of 'H'. The reason of easily measuring the value of "X" through the naked eyes is because "X1" and the height "X2" of the indicator 158 are segmented by a very short height such as 1.5 mm and the indicator 158 or the like has a distinctive color. Further, one initial drill 170 of the initial drill set 310 may be used to perform the drilling operation as deep as desired.

The subsequent procedures are the same as the typical surgical implantation procedure, and thus descriptions thereof will be omitted.

FIGS. 8A and 8B are schematic views for explaining examples of performing a guided bone regeneration procedure according to an embodiment of the present invention due to a bony defect.

For instance, if a lot of bone has to be harvested, the bone pen having the diameter of 10 mm is used to perform decortification and forms a drilling hole 160a. In this case, the drill section 111 has a diameter of 2.8 mm and a maximum depth of 4.3 mm.

As described above, it is possible to provide a bone pen, a bone pin, a bone pen set, a bone pin set and a bone pen kit including the same and an initial drill, which have a shape and size corresponding to an average shape of each target tooth, harvest bones while easily and conveniently marking and drilling the center of the target tooth, and are standardized to be optimized corresponding to various sizes of the target tooth.

Also, it is possible to provide a bone pen, a bone pin, a bone pen set, a bone pin set and a bone pen kit including the same and an initial drill, which are convenient for operations of a series of target teeth, and easily determine height of a prosthesis and drilling depth of a fixture or the like.

Also, it is possible to provide a bone pen, a bone pin, a bone pen set, a bone pin set and a bone pen kit including the same and an initial drill, in which the minimum set of instruments corresponding to serial operations and various target teeth is provided to thereby improve convenience and economic feasibility, damage to a gingiva or an alveolar bone is minimized while drilling or harvesting a bone, and a surgical operation is improved in reliability, accuracy and economic feasibility.

Although a few exemplary embodiments have been shown and described, it will be appreciated by those skilled in the art that changes may be made in these exemplary embodiments without departing from the principles and spirit of the invention. The scope of the invention is defined in the appended claims and their equivalents.

What is claimed is:

1. An implant surgical guide apparatus comprising:
a bone pen which is standardized by various diameters based on mesio-distal distances of natural teeth so that an implant can be placed at the center of a prosthetics, and comprises a cup having a rotatably symmetrical shape and a pen coupled to the cup and comprising a drill section provided at an end portion thereof for drilling into an alveolar bone so that the implant can be guided to a position with an angle as desired by an operator when the implant is placed in the alveolar bone corresponding to tooth loss,
wherein the cup is rotatably coupled with the pen so that the cup can rotate when the section rotates.

2. The implant surgical guide apparatus according to claim 1, further comprising a bone pin which comprises a cap having a size corresponding to the cup, and is usable as being inserted in the position drilled by the pen.

3. The implant surgical guide apparatus according to claim 2, wherein the Nth bone pin having the Nth cap is inserted in the Nth drilled position to guide an (N+1)th implant to be placed, and
the (N+1)th bone pen having the (N+1)th cup drills a position to place the (N+1)th implant while being in contact with the Nth bone pin (where, N is an integer including 1, 2, 3, . . . , N).

* * * * *